(12) United States Patent
Frerichs et al.

(10) Patent No.: US 8,759,981 B2
(45) Date of Patent: Jun. 24, 2014

(54) METHOD FOR THE PRODUCTION OF A FIXED CONNECTION BETWEEN TWO LAYERS OF A MULTILAYER SYSTEM, AND MULTILAYER SYSTEM

(75) Inventors: Heinz Peter Frerichs, St. Peter (DE); Herbert Verhoeven, Kusterdingen (DE)

(73) Assignee: Micronas GmbH, Freiburg (DE)

( * ) Notice: Subject to any disclaimer, the term of this patent is extended or adjusted under 35 U.S.C. 154(b) by 3476 days.

(21) Appl. No.: 10/524,672

(22) PCT Filed: Aug. 12, 2003

(86) PCT No.: PCT/EP03/08913
§ 371 (c)(1),
(2), (4) Date: Feb. 28, 2007

(87) PCT Pub. No.: WO2004/022332
PCT Pub. Date: Mar. 18, 2004

(65) Prior Publication Data
US 2007/0161209 A1 Jul. 12, 2007

(30) Foreign Application Priority Data
Aug. 13, 2002 (DE) .................................. 102 37 013

(51) Int. Cl.
*H01L 23/48* (2006.01)
(52) U.S. Cl.
USPC .................... 257/774; 257/E23.001; 438/622
(58) Field of Classification Search
USPC ........................... 257/774, E23.001; 438/622
See application file for complete search history.

(56) References Cited

U.S. PATENT DOCUMENTS

| | | | |
|---|---|---|---|
| 4,610,042 A | 9/1986 | Theodorsen | 12/142 |
| 5,476,003 A | 12/1995 | Neumann | 73/31.06 |
| 6,060,009 A | 5/2000 | Welygan et al. | 47/6 |
| 2003/0032288 A1 | 2/2003 | Kozaki et al. | 438/689 |

FOREIGN PATENT DOCUMENTS

| | | | |
|---|---|---|---|
| DE | 2821303 | 10/1980 | 3/2 |
| DE | 4240996 | 6/1994 | 7/20 |
| EP | 0875360 | 11/1998 | 59/16 |
| JP | 2002158447 A | * 5/2002 | |

* cited by examiner

*Primary Examiner* — Thao X Le
*Assistant Examiner* — Matthew Gordon
(74) *Attorney, Agent, or Firm* — Muncy, Geissler, Olds & Lowe, PLLC

(57) ABSTRACT

A multilayer system includes first and second functional layers, for example, semiconductor layers. A third or intermediate layer is disposed between the first and second functional layers and adheres relatively well to the first and second layers yet has relatively little or no detrimental effect on the functionality of the first and second layers. The third layer is applied to the first layer. Anchoring elements are provided which are partly embedded in the third layer, and the second layer is secured to the third layer by the anchoring elements. This structure yields good adhesion between the three layers, because the third layer adheres relatively well to the first layer and the third layer and the second layer are mechanically bonded together relatively strongly by the anchoring elements.

14 Claims, 3 Drawing Sheets ly patented to a second patented to the metal coating, and the metal coating enters into a stronger bond with the substrate because of the increased surface area of the
METHOD FOR THE PRODUCTION OF A FIXED CONNECTION BETWEEN TWO LAYERS OF A MULTILAYER SYSTEM, AND MULTILAYER SYSTEM

PRIORITY INFORMATION

This patent application claims priority from German Application No. 102 37 013.3 filed Aug. 13, 2002 and International Application No. PCT/EP2003/008913 filed Aug. 12, 2003, which are hereby incorporated by reference.

BACKGROUND OF THE INVENTION

The invention relates in general to semiconductors and in particular to a method for securely bonding together first and second functional layers of semiconductors. Multilayer systems comprise at least two mutually adhering layers and serve, for example, as sensors for detecting substances such as gases. Those layers that detect the substance are typically referred to as functional layers.

A disadvantage of such functional layers is that they may not adhere together with sufficiently high strength. For this reason, an additional intermediate layer yielding a greater adhesive action may be inserted between the two functional layers. However, the intermediate layer may have the disadvantage in that this layer may diminish the functionality of the functional layers.

In the case of a hydrogen sensor, for example, adequate measuring accuracy requires the cleanest possible interface between one functional layer made of, for example, palladium and another functional layer made of, for example, silicon nitrite. However, these two materials comprising the functional layers generally do not adhere together relatively well. As a result, disposed between these two functional layers is usually an intermediate layer which adheres relatively well to both functional layers. Nickel may be used as the intermediate layer to adhere the two functional layers of the hydrogen sensor together. However, the use of nickel typically impairs the functionality of a hydrogen sensor to some degree.

Thus, in general, the functional layers should adhere strongly together, yet their functionality should not be impaired.

As a result of this tradeoff, the method described in German patent DE 42 40 996 C1 is not generally applicable. Therein, two layers are bonded using a layer of adhesive applied therebetween, which is passed through in pointwise fashion by islands of fast-setting hot-melt adhesive. These adhesive islands fix the layers with respect to one another until the layer of adhesive applied in a large-area manner takes effect. With macroscopically thick layers of adhesive, this method is well-suited to the bonding of circuit arrangements to a circuit board, but less suitable to the use of functional layers, because the thick layers of adhesive may impair the functionality of the components. Further, this method presupposes that a material is known with which a firm bond can be produced between the various layers.

German patent application DE 28 21 303 B1 describes a method for bonding an insulating substrate to a metal coating, where the insulating substrate has a certain chemical composition. The chemical composition makes possible a selective etching operation by which depressions are made in the insulating substrate, thereby increasing its surface area. Afterward, a metal coating is deposited on the substrate in a currentless manner. The metal coating enters into a stronger bond with the substrate because of the increased surface area of the substrate. This method has the disadvantage that it is utilized with only those layer systems in which the requisite adhesive force can be achieved through an increase in the adhesion area. If the materials of the two layers do not generally adhere to one another, or if the requisite adhesive force is not attained even after the increase in the surface area, then this method does not achieve the desired success.

Similarly, the method described in German patent application DE 197 18 177 A1 utilizes an increase in the surface area of a substrate layer to improve the adhesion between this substrate and a second layer to be applied. Therein the substrate surface area is increased by first applying opaque particles to the substrate surface, which masks the substrate surface. Next, material is stripped off in the unmasked regions of the substrate surface, for example by a laser. This has the effect of roughening the substrate surface. After the masked particles are removed, the second layer is applied to the substrate surface and, because of the increased adhesion area, a stronger bond between the two layers results. This method has the advantage that when the material-stripping light is obliquely incident, webs remain on the substrate surface, which webs narrow toward the substrate surface. If the second layer is subsequently applied to the substrate, a type of keying interlocking results between the substrate and the second layer. This results in enhanced adhesion and, in particular, bonding between two layers that may otherwise not adhere to one another. Due to features of the method, the webs serving as anchoring elements may be made of the same material as the substrate. As a consequence, if the layer to be applied adheres poorly or not at all to the substrate, it may be necessary to provide a relatively high number of wedge-shaped webs or anchoring elements to ensure adequate adhesion between the layers to be bonded. If the webs are not fashioned in wedge shape, a strong adhesive bonding of the layers may not be possible.

What is needed is a method for producing a relatively strong bond between two functional layers of a semiconductor while at the same time allowing for a relatively high degree of functionality of the layers.

SUMMARY OF THE INVENTION

A multilayer semiconductor includes first and second functional layers. A third or intermediate layer is disposed between the first and second functional layers and adheres relatively well to the first and second layers yet has relatively little or no detrimental effect on the functionality of the first and second layers. The third layer is applied to the first layer. Anchoring elements are provided which are partly embedded in the third layer, and the second layer is secured to the third layer by the anchoring elements. This structure yields good adhesion between the three layers, because the third layer adheres relatively well to the first layer and the third layer and the second layer are mechanically bonded together relatively strongly by the anchoring elements.

In a method for binding together the first and second functional layers, to the first layer is applied, at least partially, a third layer in which a plurality of holes are formed. The holes can be formed in the third layer by, for example, an etching process or a photoetching process. The holes may be filled with an adhesive compound. Excess adhesive compound issuing from the holes is removed, for example by etching. The third layer may then be stripped down to a predetermined thickness, for example by an etching process or a photoetching process. After etching the third layer, anchoring elements formed from the adhesive compound protrude from the third layer. The second layer may then be applied to the third layer after which the anchoring elements are embedded in both the third layer and the second layer. The result is that the second layer is securely bonded to the third layer.

The holes in the third layer and also the anchoring elements formed from the adhesive compound can be cylindrical in shape. However, a relatively stronger degree of anchoring can be achieved if the cross-sectional area of a hole and a corresponding anchoring element increases or decreases from one end to the other end (e.g., tapered). For example, the cross-sectional area of the hole and of the anchoring element may increase from the third layer end to the second layer end. The result is that the anchoring elements have a conical or double conical shape, which mechanically interlocks the anchoring elements with the second layer. This is advantageous when the adhesive compound does not adhere to the second layer, so that bonding of the second and third layers may not be possible without interlocking.

The two functional layers can be bonded together in various ways. For example, if the second and third layers are the functional layers, then the third layer can be etched back to the extent this layer retains a thickness adequate for the functional layer. The first layer in this example is a substrate that may serve, for example, if the holes are made in the third layer by an etching process, to stop the etching process as soon as the holes pass through the third layer from the top of the third layer to the bottom. Also if the adhesive compound forming the anchoring elements adheres not to the third layer but to the first layer, then the anchoring elements adhering to the first layer and embedded in the second layer create a bond between the first layer and the second layer. This also simultaneously results in a strong bond between the third layer and the second layer. On the other hand, if the material comprising the anchoring elements adheres adequately to the third layer, then the holes may not pass through the third layer. As such, the holes for example can be of conical shape. In this case, to the extent that the first layer is not required for stopping any etching process, the first layer may not be needed.

If the first and second layers comprise the functional layers and the material used for the anchoring elements adheres adequately to the first layer, then the third layer can be completely removed after the holes have been filled with the adhesive compound. The first layer and the second layer are then bonded together by the anchoring elements without the intermediate third layer.

Also, if the first and second layers comprise the functional layers and the material used for the anchoring elements adheres to neither of these two layers, then the third layer may comprise a material that enters into a strong bond both with the first layer and with the anchoring elements. After the anchoring elements have been formed, the third layer may be etched back to a predetermined thickness depending on the required bond strength. The anchoring elements may be formed such that their cross-sectional area decreases toward the first layer such that, with the use of the interlocking effect, a strong bond is formed between the anchoring elements or the third layer and the second layer, and thus also between the second layer and the first layer.

Also, there may be a region free of the third layer, in which region the first and second functional layers directly adjoin one another. In this example, the third layer and corresponding anchoring elements may be located outside of this free region. As such, the anchoring elements located outside the free region provide for good adhesion of all of the layers throughout.

The third layer may comprise a material that enters into a strong physical or chemical bond with the first layer or the second layer but may impair the functionality of the two layers to a relatively small degree. Along with mechanical anchoring, the selection of the material for the anchoring elements can also increase the adhesion of the second functional layer.

A dielectric is suitable for the third layer. The conical shape of the anchoring elements is achieved for example with the aid of texturing methods that give well-defined weight to anisotropic and isotropic texturing.

The method may be used for example for fabricating sensors comprising a plurality of layers, but it is not limited as such. Conductive layer bonds with strong adhesion may be produced, such as for example bond pads for semiconductors. Bond pads are commonly fabricated from aluminum, and as such, the temperature in subsequent manufacturing process steps typically does not exceed 400° C. This is particularly applicable in the case of methods for manufacturing semiconductor sensor chips. The method is not, however, limited to the use of bond pads made from aluminum. Alternative materials may be utilized.

These and other objects, features and advantages of the present invention will become more apparent in light of the following detailed description of preferred embodiments thereof, as illustrated in the accompanying drawings.

DETAILED DESCRIPTION OF THE INVENTION

Figure 1:
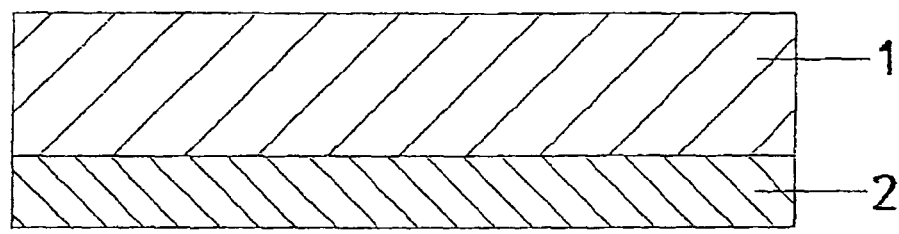
FIG. 1 is a cross-sectional illustration of a first functional layer and a dielectric layer joined together.
Figure 2:
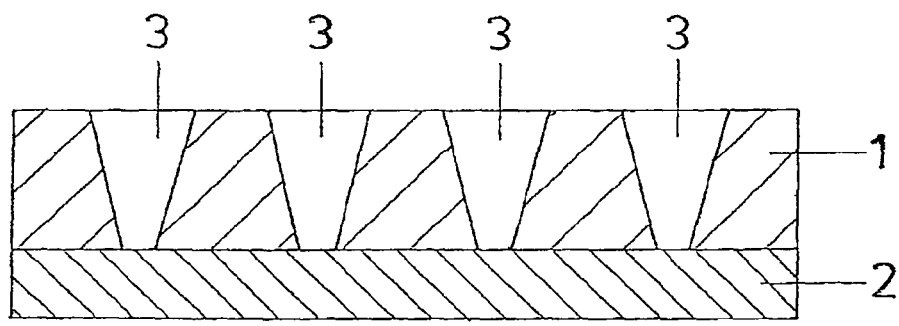
FIG. 2 is a cross-sectional illustration of the first functional layer and dielectric layer of FIG. 1, where the dielectric layer has holes formed therein.

Referring to FIG. 1, a dielectric layer 1 is applied to a first functional layer 2. As illustrated in FIG. 2, a plurality of holes 3, for example in conical or double conical shape, are formed in the dielectric layer 1. The holes 3 are formed, for example, by an etching process or a photoetching process.

Figure 3:
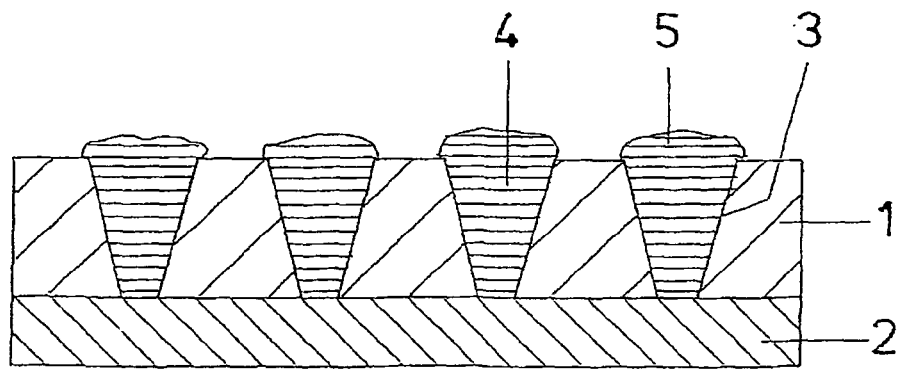
FIG. 3 is a cross-sectional illustration of the first functional layer and the dielectric layer of FIG. 2, where the holes have been filled with adhesive compound.
Figure 4:
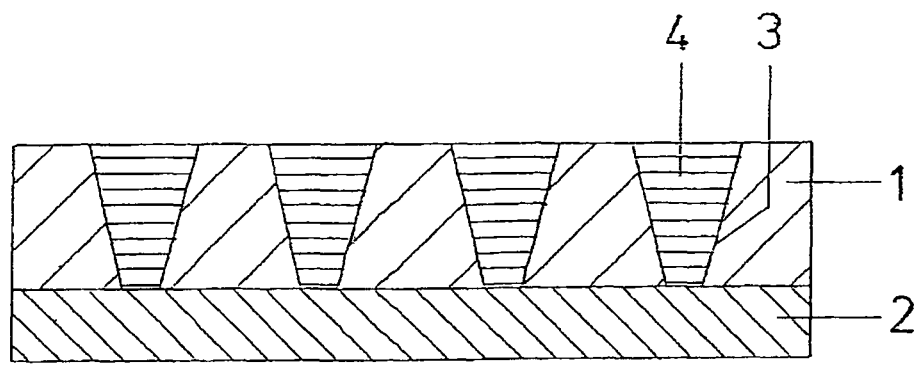
FIG. 4 is a cross-sectional illustration of the first functional layer and the dielectric layer of FIG. 3 with the holes filled with adhesive compound, where excess adhesive compound has been removed.

In FIG. 3, the holes 3 are filled with an adhesive compound 4. Excess adhesive compound 5 issuing from holes 3 is removed, for example, by an etching process. FIG. 4 illustrates the functional layer 2 and the dielectric layer 1 with the holes 3 filled with adhesive compound 4, and after any excess adhesive compound 5 has been etched away.

Figure 5:
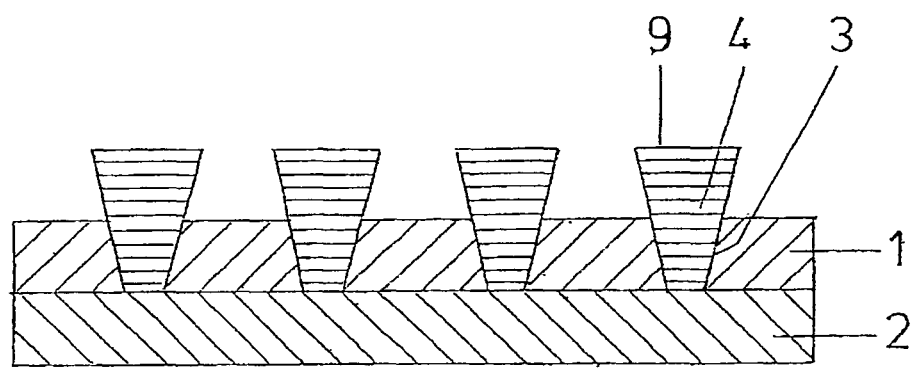
FIG. 5 is a cross-sectional illustration of the first functional layer and the dielectric layer of FIG. 4 with a portion of the dielectric layer etched away thereby forming anchoring elements from the adhesive compound.

Referring to FIG. 5, the dielectric layer 1 undergoes an for example by an etching or photoetching process to expose anchoring elements 9 formed from the adhesive compound 4.

Figure 6:
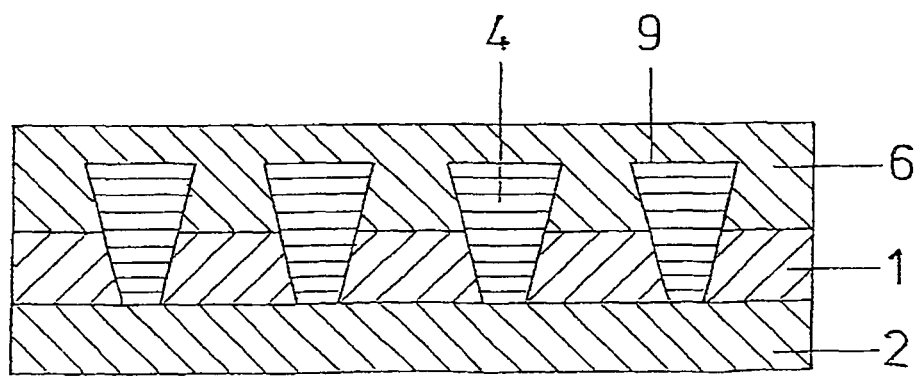
FIG. 6 is a cross-sectional illustration of the first functional layer and the dielectric layer of FIG. 5, also having a second functional layer and anchoring elements interlocking the dielectric layer and the second functional layer together.

In FIG. 6, a second functional layer 6 is applied to the dielectric layer 1. As a result, the anchoring elements 9 are embedded in both the dielectric layer 1 and the second functional layer 6, thereby bonding the second functional layer 6 relatively strongly to the dielectric layer 1.

A dielectric material is suitable as this third layer or intermediate layer 1, because such material typically does not impair the functionality of the functional layers 2, 6.

Figure 7:
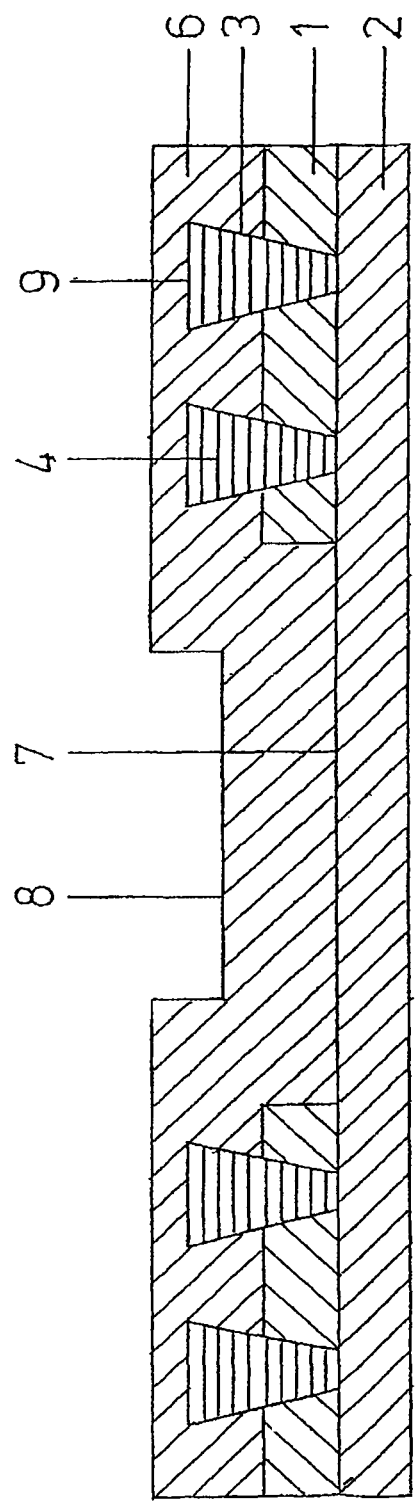
FIG. 7 is a cross-sectional illustration of a multilayer semiconductor having a functional region with no dielectric.

Referring to FIG. 7, the multilayer semiconductor illustrated there differs from that illustrated in FIG. 6 in that there is a region 8 that is free of the dielectric layer 1. The first functional layer 2 and the second functional layer 6 directly adjoin one another in this region 8. As such, a higher degree of functionality may be achieved in the region 8 without any loss of adhesion. The dielectric layer 1 and the anchoring elements 9 formed from adhesive compound 4, which are embedded both in the dielectric layer 1 and in the second functional layer 6, are arranged next to the region 8 on both sides thereof, as illustrated in FIG. 7.

Figure 8:
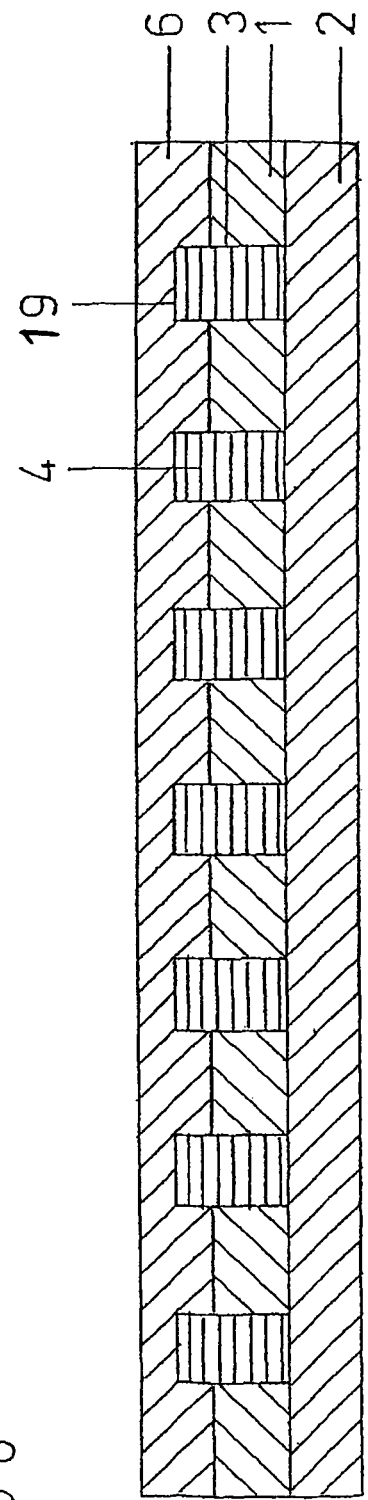
FIG. 8 is a cross-sectional illustration of a multilayer semiconductor having cylindrical anchoring elements.

Referring to FIG. 8, the dielectric layer 1 is applied to the first functional layer 2, and the second functional layer 6 is adjacent the dielectric layer 1. The anchoring elements 19 formed from the adhesive compound 4 are embedded both in the dielectric layer 1 and in the second functional layer 6. The anchoring elements 19 are cylindrical in shape and as such may be produced more easily than conically shaped anchoring elements 19. However, the degree of interlocking achieved with the cylindrical anchoring elements 19 may not be as strong as with the conically shaped anchoring elements.

As discussed hereinabove, the teachings herein may be suitable, without limitation, for multilayer sensors and for conductive layer bonds in semiconductor technology. In semiconductor technology, bond pads can be fabricated similar to the multilayer semiconductors of FIGS. 1-8 at process temperatures above 400° C. The filling compound for forming the anchoring elements may comprise the element tungsten. The conductive layers, which correspond to the functional layers, are fabricated for example from a noble metal.

Values between 100 and 1000 nm may be suitable dimensions for the diameter and spacing of the anchoring elements. The layer thicknesses may also be between 100 and 1000 nm. The anchoring elements may protrude some 20 to 500 nm from the top of the dielectric layer.

Although the present invention has been shown and described with respect to several preferred embodiments thereof, various changes, omissions and additions to the form and detail thereof, may be made therein, without departing from the spirit and scope of the invention.

What is claimed is:

1. A multilayer semiconductor sensor, comprising:
a first functional layer;
a second functional layer;
an intermediate layer disposed between the first and the second functional layers in a first predetermined region; and
a plurality of anchoring elements each embedded in at least two of the first and the second functional layers and the intermediate layer, where the anchoring elements comprise a different material than that of the first and the second functional layers.

2. The multilayer semiconductor sensor of claim 1, where each of the plurality of anchoring elements is embedded in the second functional layer and in the intermediate layer.

3. The multilayer semiconductor sensor of claim 1, where a cross-sectional area of each of the plurality of anchoring elements is cylindrical.

4. The multilayer semiconductor sensor of claim 1, where a cross-sectional area of each of the plurality of anchoring elements increases from one end of the anchoring element to the other end of the anchoring element.

5. The multilayer semiconductor sensor of claim 1, where each of the plurality of anchoring elements has a conical shape.

6. The multilayer semiconductor sensor of claim 1, where the first and the second functional layers adjoin each other in a second predetermined region that is outside the first predetermined region.

7. The multilayer semiconductor sensor of claim 1, where the intermediate layer is adhered to the first functional layer.

8. The multilayer semiconductor sensor of claim 1, where a diameter of each of the plurality of anchoring elements lies in a range between 100 and 1000 nm.

9. The multilayer semiconductor sensor of claim 1, where a spacing between the plurality of anchoring elements lies in a range between 100 and 1000 nm.

10. The multilayer system of claim 1, where each of the plurality of anchoring elements is embedded into the second functional layer at a depth of between 20 and 500 nm.

11. The multilayer semiconductor sensor of claim 1, where a thickness of each of the first and the second functional layers lies in a range between 100 and 1000 nm.

12. The multilayer semiconductor sensor of claim 1, where the intermediate layer comprises a dielectric material.

13. A multilayer semiconductor, comprising:
a first functional layer;
a second functional layer coupled to the first functional layer; and
a plurality of anchoring elements disposed between, and partially embedded in at least one of the first and the second functional layers, where the anchoring elements comprise a different material than that of the first and the second functional layers.

14. The multilayer semiconductor of claim 13, further comprising an intermediate layer disposed between the first and the second functional layers, where the plurality of anchoring elements are partially embedded in the intermediate layer.

* * * * *